United States Patent [19]
Gagnebien et al.

[11] Patent Number: 5,888,951
[45] Date of Patent: Mar. 30, 1999

[54] FOAMING COMPOSITION FOR CLEANING THE SKIN

[75] Inventors: Didier Gagnebien, Westfield, N.J.; Pascal Simon, Vitry sur Seine, France

[73] Assignee: L'Oreal, Paris, France

[21] Appl. No.: 962,445

[22] Filed: Oct. 31, 1997

[30] Foreign Application Priority Data

Nov. 4, 1996 [FR] France ................... 96 13405

[51] Int. Cl.⁶ .............. A61K 7/02; A61K 7/06; A61K 7/48; A61K 7/50
[52] U.S. Cl. ........... 510/130; 510/137; 510/138; 510/158; 252/367.1
[58] Field of Search ................. 510/130, 135, 510/137, 138, 158, 159; 252/367.1

[56] References Cited

U.S. PATENT DOCUMENTS

| | | | |
|---|---|---|---|
| 4,268,498 | 5/1981 | Gedeon et al. | 424/59 |
| 4,482,537 | 11/1984 | El-Menshawy et al. | 424/59 |
| 4,687,843 | 8/1987 | Smolin et al. | 536/18.3 |
| 4,933,176 | 6/1990 | van Reeth | 424/70 |

FOREIGN PATENT DOCUMENTS

| | | |
|---|---|---|
| 0 274 812 | 7/1988 | European Pat. Off. . |
| 0 588 379 A | 3/1994 | European Pat. Off. . |
| 2 237 615 A | 2/1975 | France . |
| 41 39 935 A | 6/1993 | Germany . |
| WO 92/07543 | 5/1992 | WIPO . |
| WO 93/08840 | 5/1993 | WIPO . |
| WO 94/17830 | 8/1994 | WIPO . |

OTHER PUBLICATIONS

Chemical Abstracts, vol. 93, No. 18, Nov. 3, 1980, pp. 344–345.

*Primary Examiner*—Nathan M. Nutter
*Attorney, Agent, or Firm*—Oblon, Spivak, McClelland, Maier & Neustadt, P.C.

[57] ABSTRACT

Foaming composition for cleaning the skin, which has the appearance of a transparent gel, including:

(i) a fatty phase,
(ii) at least one $C_5$–$C_7$ carbohydrate fatty ester,
(iii) at least one polyol,
(iv) at least one foaming surfactant.

22 Claims, No Drawings

FOAMING COMPOSITION FOR CLEANING THE SKIN

BACKGROUND OF THE INVENTION

1. Field of the Invention

The invention relates to foaming compositions for cleaning the skin which preferably are rich in oils, gelled in appearance, transparent and water-rinsable.

2. Discussion of the Background

Cleaning the skin is very important for face care. It must be as effective as possible because the fatty residues such as excess sebum, residues of the cosmetic products which are employed daily, and make-up products, especially the water-resistant "waterproof" products, accumulate in skin folds and at the surface of the skin and can block skin pores and entail the appearance of spots. Poor cleaning quality, and in particular poor rinsing, are often responsible, among other causative factors, for a sallow complexion.

A number of major types of products for cleaning the skin are known: lotions and foaming detergent aqueous gels and oils and rinsable cleaning anhydrous gels, milks for removing make-up, and foaming creams which are usually soap-based.

The lotions and the foaming detergent aqueous gels have a cleaning action by virtue of the surfactants which place the fatty residues and the pigments of the make-up products in suspension. They are effective and cosmetically pleasant because they foam and because they are easily removed. Insofar as they do not contain any cosmetic oil, they have the disadvantage of making the skin dry owing to their lipid-removing action.

This is the case, for example, with the products described by document WO 95/05769, which teaches lotions for cleaning the skin, which are very fluid, pressurizable and which produce a beautiful foam, but these products destroy the hydrolipid film of the skin and leave the skin clean but rough.

The creams and the milks for removing make-up contain, at the same time, oils, emulsifiers and detergent surfactants in a quantity which is sufficiently low not to destabilize the emulsion. Despite their good effectiveness, these products are not foaming and have an insufficient rinsability which requires the use of a complementary detergent tonic lotion to complete the rinsing and the removal of the soiling. Besides its astringent character, the use of this second product can in the long term result in making the skin dry.

In the field of skin cleaning, the removal of make-up of water-resistant "waterproof" products, of transfer-free products and of heavy make-ups, like stage make-ups, requires the use of oily compounds to be effective.

Oily compositions are recognized for their effectiveness as a cleaning agent and/or make-up remover. They in fact allow lipophilic soiling and make-up to be dissolved very easily, in particular the "waterproof" and transfer-free make-ups which are known to be difficult to remove. These products are effective and well tolerated. They have the disadvantage of not foaming and not imparting a feeling of coolness on application, and this is a disadvantage from a cosmetic viewpoint. Besides, the oily compositions which have the appearance of a gel are usually thickened with waxes, silicas, modified clays or polyvalent salts of fatty acids, which give them an appearance that is usually turbid or opaque and not very attractive; their stability over time is often limited.

Attempts have been made to design cleaning foaming products which are perfectly rinsable with water, including oils in large quantities so as to optimize the cleaning of the skin and to hydrate and nourish the latter while avoiding any phenomenon of drying out and of irritation. In addition, attempts have been made to prepare compositions which have an attractive appearance, that of a transparent gel, these compositions being easily removed by rinsing with water and being perfectly stable in storage.

To produce such a product it is not possible merely to introduce oils into a lotion or an aqueous gel. In fact, oils have a tendency to inhibit the foaming properties of these formulations; it is said that the oils "kill" the foam.

SUMMARY OF THE INVENTION

The subject-matter of the invention is compositions for cleaning the skin which have the appearance of, or include, a stable, foaming transparent gel. These compositions are characterized by the fact that they include:

(i) a fatty phase,
(ii) at least one $C_5$–$C_7$ carbohydrate fatty ester,
(iii) at least one polyol, and
(iv) at least one foaming surfactant.

Methods of treating the skin, including cleansing, with invention compositions also make up part of the invention.

As used herein the word "transparent" means that through a transparent bottle containing the invention composition it is possible to distinguish the characters printed on a newspaper page placed behind this bottle. Preferably, the transparent bottle has a thickness of 6–12 cm.

The viscosity of the compositions according to the invention is preferably higher than 2 Pa s, more preferably higher than 4 Pa s and still more preferably higher than 5 Pa s including 8, 10, 12, 15, 20 and 23 Pa s. It is preferably lower than 25 Pa s. This viscosity is determined at room temperature (20–25° C.) and room pressure, with RHEOMAT 180 (METTLER) with a measure body at 200 rpm.

Oily compositions for cleaning the skin, in the form of a stable transparent gel including a hydrophilic sucrose fatty ester and a polyol were known in the prior art, for example from documents JP-5-229916 and JP-60-115509, it being possible for these compositions to include a foaming surfactant. However, these compositions have a number of disadvantages: such sucrose derivatives are characterized by a high instability to temperature and are preferably absent from the invention compositions; the compositions described in these documents include low percentages of foaming surfactant in relation to their percentage of oil, this small proportion of foaming agent not allowing them to form a foam; when the percentage of foaming surfactant in these compositions is increased, a dephased, opaque, unstable mixture is obtained, as will be shown in the comparative tests.

The compositions according to the invention overcome the disadvantages of the prior art. These compositions and their astonishing properties were neither mentioned nor suggested in the prior art.

Invention compositions also preferably include water. In this case they are advantageously in the form of an oil-in-water emulsion which has the appearance of a gel.

$C_5$–$C_7$ carbohydrates as used herein are intended to mean pentoses, hexoses and heptoses (not reduced) and their alkyl holoside derivatives in which the alkyl group contains from 1 to 6 carbon atoms. The carbohydrates are advantageously chosen from those which have a chain containing 6 carbon atoms and they are preferably chosen from glucose, fructose and their $C_1$–$C_6$ alkyl glucoside and alkyl fructoside derivatives. Still more preferably the carbohydrate is glucose or an alkyl glucoside derivative like, for example, 1-methyl-glucoside.

$C_5$–$C_7$ carbohydrate fatty esters as used herein is intended to mean preferably the compounds obtained by reaction of a fatty acid containing a saturated or unsaturated chain containing from 8 to 30 carbon atoms, preferably from 12 to 22 carbon atoms, and still more preferably from 16 to 20 carbon atoms, with a carbohydrate chosen from pentoses, hexoses, heptoses and their alkyl holoside derivatives in which the alkyl group contains from 1 to 6 carbon atoms.

The carbohydrate fatty acid ester may contain a mixture of mono-, di-, tri- and tetraester derivatives.

The $C_5$–$C_7$ carbohydrate fatty esters are advantageously oxyalkylenated. The $C_5$–$C_7$ carbohydrate esters are preferably etherified by one or more oxyethylene or oxypropylene fragments, the total of the oxyethylene or oxypropylene substituents representing in all from 5 to 200 and preferably 15 to 150 alkylene oxide units.

All the hydroxyl functional groups of the carbohydrate derivatives employed in the compositions according to the invention may be advantageously substituted by an ester group or by an alkylene oxide group.

Such compounds are well known to a person skilled in the art. A number of these compounds are available commercially. It is possible, for example, to employ the derivatives sold under the trade name Glucamate by Amerchol.

The $C_6$ carbohydrate fatty esters of the invention are preferably chosen from the compounds corresponding to the formula (I):

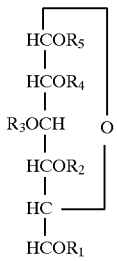 (I)

in which $R_1$ is a group of formula (III):

 (III)

R' being chosen from $C_8$–$C_{30}$ and preferably $C_{12}$–$C_{22}$ saturated or unsaturated, linear or branched alkyl groups, $R_2$, $R_3$ and $R_4$, which are identical or different, denote a group chosen from:
a hydrogen atom,
a group of formula (II):

 (II)

with n=2 or 3; p is an integer ranging from 2 to 50; R denotes a hydrogen atom or a $C_1$–$C_6$ alkyl group,
a group of formula (III):

—OC—R' (III)

R' being chosen from $C_8$—$C_{30}$ and preferably $C_{12}$–$C_{22}$ saturated or unsaturated, linear or branched alkyl groups, at least one of $R_2$, $R_3$ and $R_4$ being a group of formula (II), the total of the oxyalkylene residues, $\Sigma p$, being between 5 and 200, $R_5$ being a saturated or unsaturated, linear or branched $C_1$–$C_6$ alkyl group.

The choice is preferably:
$R_5$=$CH_3$,
at least two groups from $R_2$, $R_3$ and $R_4$ correspond to the formula (II),
$\Sigma p$ is between 15 and 150,
R=H,
R' is chosen from $C_{16}$–$C_{20}$ alkyl groups,
none of the groups $R_2$, $R_3$ and $R_4$ is the hydrogen atom.

The compositions according to the invention advantageously include, by weight relative to the total weight of the composition, from 0.5 to 50% of $C_5$–$C_7$ carbohydrate fatty ester, and preferably from 2 to 20% including 5, 10 and 15%.

The compositions according to the invention include at least one polyol. This polyol may optionally be oxyalkylenated. The polyol advantageously includes at least two free hydroxyl functional groups. This polyol may be chosen from ethylene glycol, propylene glycol, 1,3-butylene glycol, dipropylene glycol, glycerine, polyglycerines like diglycerine, triglycerine and tetraglycerine, glucose, maltose, maltitol, sucrose, fructose, sorbitol, sugars originating from the decomposition of starch and mixtures thereof.

The polyol represents advantageously from 0.5 to 60% by weight relative to the total weight of the composition, preferably from 2 to 40% and still more preferably from 5 to 30% including 10, 20 and 25%.

The nature of the fatty phase forming part of the composition of the emulsions according to the invention is not critical; it may thus consist of any of the compounds that are already generally known as suitable for the manufacture of emulsions of oil-in-water type. In particular, these compounds may be chosen, alone or as mixtures, from the various fatty substances, oils of vegetable, animal or mineral origin, natural or synthetic waxes and the like.

Oils that can be employed in the present invention include oils of vegetable or animal origin like, for example, squalane, copra oil, macadamia oil, mink oil, turtle oil, soya oil, grape seed oil, sesame oil, corn oil, rapeseed oil, sunflower oil, cotton oil, avocado oil, olive oil, castor oil, jojoba oil and groundnut oil; hydrocarbon oils such as paraffin oils, petrolatum, isododecane, isohexadecane, isoparaffins; silicone oils like polydimethylsiloxanes, cyclopolydimethylsiloxanes, polymethylphenylsiloxanes, polysiloxanes modified with fatty acids, polysiloxanes modified with fatty alcohols, polysiloxanes modified with polyoxyalkylenes and fluoro silicones; perfluoro and/or organofluoro oils; higher fatty acids such as myristic acid, palmitic acid, stearic acid, behenic acid, oleic acid, linoleic acid, linolenic acid, isostearic acid, higher fatty alcohols such as cetanol, stearyl alcohol and oleyl alcohol; mono- and diesters among which there may be mentioned in particular isopropyl myristate, isopropyl palmitate, butyl stearate, hexyl laurate, isononyl isononanoate, 2-ethylhexyl palmitate, 2-hexyldecyl laurate, 2-octyldecyl palmitate, 2-octyldodecyl myristate, di-2-ethylhexyl succinate, diisostearyl malate, 2-octyldodecyl lactate, glycerine triisostearate, di-n-butyl adipate, di(2-ethylhexyl) adipate, ethylene glycol dioleate, ethylene glycol diisotridecanoate, ethylene glycol diisostearate and neopentyl glycol dicaprylate.

An oil or a mixture of oils which has a refractive index $^{20}n_D \leq 1.45$ is preferably employed.

The fatty phase may represent from 1 to 95% by weight of the total weight of the composition, preferably from 20 to 85% and still more preferably from 40 to 80%.

The compositions according to the invention include at least one foaming surfactant. See "Encyclopedia of Chemical Technology, Kirk-Othmer", Volume 22, p. 333–432, 3rd edition, 1979, Wiley, incorporated herein by reference where the chief classes of surfactants known to a person skilled in the art, and their functions (in particular the fact of being foaming), are cited.

The foaming surfactants employed according to the present invention preferably are chosen from surfactants which have a foaming power characterized by a foam height greater than 100 mm, preferably greater than 120 mm, measured according to the Ross-Miles method for a solution containing 0.1% by weight of surfactant in distilled water at 25° C.

These surfactants are preferably chosen from anionic surfactants and amphoteric surfactants. Included among these classes of surfactants are the following:

amphoteric surfactants: alkylbetaines, alkylsulphobetaines, alkylamidopropylbetaines, alkali or alkaline-earth metal alkylcarboxyglycinates, imidazolines; among these classes of surfactants the following examples may be mentioned more particularly: dimethylbetaine, cocobetaine, cocoamidopropylbetaine, cocoamidopropylhydroxysultaine and disodium cocoamphodiacetate;

anionic surfactants: alkylphosphates like, for example, sodium lauryl phosphate, alkyl taurates like, for example, sodium methyl palmitoyl taurate, sulphosuccinates like, for example, cocoyl sulphosuccinate, the disodium salt of oxylenated lauryl alcohol sulphosuccinate, alkyl sulphates like, for example, triethanolamine lauryl sulphate, sarcosinates like, for example, sodium lauroyl sarcosinate, alkyl ether sulphates like, for example, sodium lauroyl ether sulphate, isethionates like, for example, sodium cocoyl isethionate and alkyl ether carboxylates like, for example, oxyethylenated sodium decyl ether carboxylate.

It is advantageously possible to provide a nonionic secondary foaming surfactant in the compositions according to the invention, to improve the qualities of the foam (density, smoothness, softness). This foaming agent may, for example, be chosen from:

the compounds of formula:

$$R^1O(G)_p \quad (II)$$

in which R' is a monovalent hydrocarbon chain containing from 1 to 30 carbon atoms, G is a saccharide derivative containing from 5 to 6 carbon atoms and p is a statistical mean value ranging from 1 to 6; the compounds of formula (II) are described especially in application WO 94/27562, incorporated herein by reference. The preferred compounds are those in which the radical $R^1$ is a $C_8$–$C_{16}$ alkyl radical and more particularly those whose degree of polymerization is 1.4 or 1.6; included, for example are:

the alkylpolyglycosides marketed by Henkel under the names APG 225, APG 425 and APG 625;

the alkylpolyglucosides marketed by Henkel under the name Glucopon, closely related to APG 625 with a different degree of polymerization;

the alkylpolyglycosides marketed by Henkel under the name Plantaren such as Plantaren 2000, which is a ($C_8$–$C_{16}$ alkyl)polyglucoside with a degree of polymerization of 1.4, Plantaren 1200, which is a ($C_{12}$–$C_{18}$ alkyl)polyglucoside of degree of polymerization 1.4, and Plantaren 1300, which is a ($C_{12}$–$C_{18}$ alkyl)polyglucoside of degree of polymerization 1.6;

the fatty acid and sorbitan oxyethylenated esters like, for example, the product marketed under the trade name Tween 20 by ICI.

The foaming surfactants may be present in a proportion of 0.5 to 50%, preferably of 2 to 40% and still more preferably of 8 to 20% by weight including 10, 15 and 18% relative to the total weight of the composition.

Water represents preferably from 0.01 to 30% by weight relative to the total weight of the composition. Water represents advantageously from 2 to 20% by weight relative to the total weight of the composition, including 5, 10 and 15%.

Water is usually intended to mean pure water. However, some of the water employed in the compositions according to the invention may optionally be chosen from among mineral or thermal waters. In general a mineral water is suitable for consumption, which is not always the case with a thermal water. Each of these waters contains, among others, dissolved minerals and trace elements. These waters are known to be employed for the purpose of specific treatment according to the trace elements and the particular minerals which they contain, such as the hydration and desensitization of the skin or the treatment of some types of dermatitis. Mineral or thermal waters will denote not only natural mineral or thermal waters, but also natural mineral or thermal waters enriched in additional mineral constituents and/or trace elements, as well as aqueous mineral and/or trace-element solutions prepared from purified water (demineralized or distilled).

Natural thermal or mineral water employed according to the invention may, for example, be chosen from among Vittel water, Vichy bassin waters, Uriage water, Roche Posay water, Bourboule water, Enghien-les-Bains water, Saint Gervais-les-Bains water, Néris-les-Bains water, Allevard-les-Bains water, Digne water, Maiziéres water, Neyrac-les-Bains water, Lons-le-Saunier water, les Eaux Bonnes water, Rochefort water, Saint Christau water, Fumades water and Tercis-les-bains water, Uriage-les-bains water and Avene water.

The compositions of the invention may additionally contain water-soluble or liposoluble adjuvants which are usual in the field of cosmetics, such as preserving agents, antioxidants, perfumes, screening agents, colorants, pearlescent agents and hydrophilic or lipophilic active substances.

They may also contain insoluble fillers: polyethylene powder, polyamide particles like, for example, those sold under the name "Orgasol" by Atochem, also known under the names (CTFA) of "polyamide 12" or "polyamide 6". It is also possible to employ in these compositions kaolin and nylon powders listed under the CTFA name of "Nylon 12" or "Nylon 6". Such compositions are advantageous in skin cleaning owing to their exfoliating properties.

The compositions according to the invention preferably have the appearance of a stable, transparent gel. In addition, these compositions have a very good rinsability. In particular, the $C_5$–$C_7$ carbohydrate fatty esters give these compositions a rinsability which is improved in relation to the compositions based on sucrose esters and those based on sorbitol esters.

The compositions according to the invention can be presented, for example, in the form of a cleaning product, make-up remover, of a hydrating product, of a deep-cleanser or of an exfoliating agent, and are used as are other products of these categories to clean the skin by washing or hydrate the skin by applying to the skin, etc.

EXAMPLES

In each composition the percentages are given as weight of active material in relation to the total weight of the composition.

The viscosity is measured at 25° C. with the aid of a Rheomat 180 viscometer and the viscosity measurements are given in Pascal seconds (Pa s).

Example 1

Body and face cleaning composition:

| Aqueous phase: | |
| --- | --- |
| Oxyethylenated methylglucose sesquistearate (20 EO) | 4.5% |
| Glycerol | 9% |
| Water | 4.5% |
| Oily phase: | |
| Liquid petrolatum | 9% |
| 2-Ethylhexyl palmitate | 13% |
| Hydrogenated isoparaffin | 8% |
| Cyclopentadimethylsiloxane | 16% |
| Isododecane | 20% |
| Perfume | q.s. |
| Preserving agent | q.s. |
| Surfactants | |
| Sodium lauryl ether sulphate | 8% |
| Oxyethylenated sorbitan monolaurate (20 EO) | 5% |

Procedure: the glucose derivative is dissolved in water and the polyols with stirring between 25° C. and 35° C. until a homogeneous viscous paste is obtained. The oily phase and then the surfactants are then introduced slowly with vigorous stirring. The product is then smoothed with the blade and freed from bubbles under vacuum.

This composition has a clear, transparent, gelled appearance and a Rheomat viscosity of 20 Pa s. This product, which is employed under the shower, allows a gentle effective cleaning. It leaves the skin smooth and clean without residue or oily film.

Example 2

Composition for removing make-up:

| Aqueous phase: | |
| --- | --- |
| Oxyethylenated methylglucose sesquisterate (20 EO) | 0.8% |
| Oxyethylenated methylglucose dioleate (120 EO) | 2.5% |
| Glycerol | 13% |
| Water | 3.5% |
| Oily phase: | |
| Liquid petrolatum | 8% |
| 2-Ethylhexyl palmitate | 22% |
| Hydrogenated isoparaffin | 7% |
| Cyclopentadimethylsiloxane | 11% |
| Isododecane | 16.5% |
| Perfume | q.s. |
| Preserving agents | q.s. |
| Surfactants | |
| Cocoamphodiacetate | 10% |
| Sodium lauroyl sarcosinate | 5% |

This composition has a clear, transparent, gelled appearance and a Rheomat viscosity equal to 12 Pa s. The spreading of the product on the skin is easy and the rinsability excellent. After rinsing, the skin is clean and feels silky and not greasy.

COMPARATIVE TESTS

To show the advantage of the compositions according to the invention in relation to the compositions of the prior art, the following tests were carried out:

Test 1: The composition of Example 1 above was reproduced, the oxyethylenated methylglucose sesquistearate (20 EO) being replaced with sucrose palmitostearate (same percentage by weight). An unstable composition is obtained, which separates into two phases after 24 hours storage.

Test 2: The composition of Example 2 above was reproduced, replacing the oxyethylenated methylglucose sesquistearate (20 EO) and the oxyethylenated methylglucose dioleate (120 EO) with sucrose palmitostearate (same percentage by weight). A fluid and opaque composition is obtained.

Obviously, numerous modifications and variations of the present invention are possible in light of the above teachings. It is therefore to be understood that within the scope of the appended claims, the invention may be practiced otherwise than as specifically described herein.

French patent application 96-13405 filed Nov. 4, 1996 is incorporated herein by reference.

What is claimed as new and desired to be secured by Letters Patent of the United States is:

1. A composition comprising:
   (i) a fatty phase,
   (ii) at least one $C_5$–$C_7$ carbohydrate fatty ester,
   (iii) at least one polyol, and
   (iv) at least one foaming surfactant.

2. The composition according to claim 1, further comprising water.

3. The composition according to claim 1, wherein a $C_1$–$C_7$ carbohydrate of the carbohydrate fatty ester is selected from the group consisting of pentoses, hexoses and heptoses and their alkyl holoside derivatives in which the alkyl group contains from 1 to 6 carbon atoms.

4. The composition according to claim 3, wherein the $C_5$–$C_7$ carbohydrate is 1-methylglucoside.

5. The composition according to claim 1, wherein the $C_5$–$C_7$ carbohydrate fatty ester is a compound obtained by reaction of a fatty acid containing a saturated or unsaturated chain containing from 8 to 30 carbon atoms with a $C_5$–$C_7$ carbohydrate.

6. The composition according to claim 1, wherein the $C_5$–$C_7$ carbohydrate fatty ester is oxyalkylenated.

7. The composition according to claim 1, wherein the $C_5$–$C_7$ carbohydrate ester is etherified by one or more oxyethylene or oxypropylene fragments, the total of the oxyethylene or oxypropylene substituents representing from 5 to 200 alkylene oxide units.

8. The composition according to claim 1, wherein the carbohydrate fatty ester includes a compound corresponding to the formula (I):

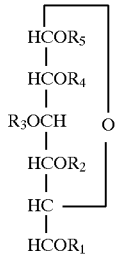

(I)

in which $R_1$ is a group of formula (III):

(III)

R' being chosen from $C_8$–$C_{30}$ saturated or unsaturated, linear or branched alkyl groups, $R_2$, $R_3$ and $R_4$, which are identical or different, denote a group selected from the group consisting of:
a hydrogen atom,
a group of formula (II):

$$—(C_nH_{2n}O)_p—R \qquad (II)$$

with n=2 or 3; p is an integer ranging from 2 to 50; R denotes a hydrogen atom or a $C_1$–$C_6$ alkyl group,
a group of formula (III):

$$—OC—R' \qquad (III)$$

R' being chosen from $C_8$–$C_{30}$ saturated or unsaturated, linear or branched alkyl groups,
at least one of $R_2$, $R_3$ and $R_4$ being a group of formula (II), the total of the oxyalkylene residues being between 5 and 200,
$R_5$ being a saturated or unsaturated, linear or branched $C_1$–$C_6$ alkyl group.

9. The composition according to claim 8, wherein
$R_5=CH_3$,
at least two groups from $R_2$, $R_3$ and $R_4$ correspond to the formula (II),
the total of the oxyalkylene residues is between 15 and 150,
R=H,
at least one group from $R_1$, $R_2$, $R_3$ and $R_4$ corresponds to the formula (III),
R' is selected from the group consisting of $C_{16}$–$C_{20}$ alkyl groups,
none of the groups $R_2$, $R_3$ and $R_4$ is a hydrogen atom.

10. The composition according to claim 1, wherein it includes, by weight relative to the total weight of the composition, from 0.5 to 50% of $C_5$–$C_7$ carbohydrate fatty ester.

11. The composition according to claim 1, wherein the polyol is selected from the group consisting of ethylene glycol, propylene glycol, 1,3-butylene glycol, dipropylene glycol, glycerine, diglycerine, triglycerine, tetraglycerine, glucose, maltose, maltitol, sucrose, fructose, sorbitol, sugars originating from the decomposition of starch and mixtures thereof.

12. The composition according to claim 1, comprising from 0.5 to 60% by weight relative to the total weight of the composition of polyol.

13. The composition according to claim 1, wherein the fatty phase includes an oil or a mixture of oils which has a refractive index $^{20}n_D \leq 1.45$.

14. The composition according to claim 1, wherein the fatty phase represents from 1 to 95% by weight of the total weight of the composition.

15. The composition according to claim 1, wherein the foaming surfactant is a surfactant which has a foaming power characterized by a foam height greater than 100 mm measured according to the Ross-Miles method for a solution containing 0.1% by weight of surfactant in distilled water at 25° C.

16. The composition according to claim 1, wherein the foaming surfactant is an anionic surfactant or an amphoteric surfactant.

17. The composition according to claim 1, wherein in the foaming surfactant is present in a quantity ranging from 0.5 to 50% by weight relative to the total weight of the composition.

18. The composition according to claim 2, wherein water represents from 0.01 to 30% by weight relative to the total weight of the composition.

19. The composition according to claim 2, wherein the water comprises Vittel water, Vichy bassin waters, Uriage water, Roche Posay water, Bourboule water, Enghien-les-Bains water, Saint Gervais-les-Bains water, Néris-les-Bains water, Allevard-les-Bains water, Digne water, Maiziéres water, Neyrac-les-Bains water, Lons-le-Saunier water, les Eaux Bonnes water, Rochefort water, Saint Christau water, Fumades water and Tercis-les-bains water, Uriage-les-bains water or Avene water.

20. The composition according to claim 1, further comprising at least one insoluble filler selected from the group consisting of kaolin, polyethylene powder, polyamide particles and nylon powder.

21. The composition according to claim 1, wherein said composition is in the form of a cleaning product, make-up remover, a hydrating product, a deep-cleanser or an exfoliating agent.

22. A method of treating the skin, comprising:
applying to the skin a composition comprising
(i) a fatty phase;
(ii) at least one $C_{5-7}$-carbohydrate fatty ester;
(iii) at least one polyol; and
(iv) and at least one foaming surfactant.

* * * * *